(12) United States Patent
Cowe et al.

(10) Patent No.: US 9,694,137 B2
(45) Date of Patent: Jul. 4, 2017

(54) INJECTION DEVICES USING A RESILIENTLY COMPRESSIBLE TORSION SPRING AS DRIVING FORCE

(71) Applicants: Toby Cowe, Oxford (GB); Simon Reitter, Gloucestershire (GB)

(72) Inventors: Toby Cowe, Oxford (GB); Simon Reitter, Gloucestershire (GB)

(73) Assignee: OWEN MUMFORD LIMITED, Oxford (GB)

( * ) Notice: Subject to any disclaimer, the term of this patent is extended or adjusted under 35 U.S.C. 154(b) by 277 days.

(21) Appl. No.: 14/400,186

(22) PCT Filed: Apr. 30, 2013

(86) PCT No.: PCT/GB2013/051100
§ 371 (c)(1),
(2) Date: Nov. 10, 2014

(87) PCT Pub. No.: WO2013/167869
PCT Pub. Date: Nov. 14, 2013

(65) Prior Publication Data
US 2015/0100029 A1    Apr. 9, 2015

(30) Foreign Application Priority Data
May 9, 2012   (GB) .................................. 1208095.8

(51) Int. Cl.
*A61M 5/20*   (2006.01)
*A61M 5/315*  (2006.01)

(52) U.S. Cl.
CPC ............ *A61M 5/3159* (2013.01); *A61M 5/20* (2013.01); *A61M 5/31583* (2013.01); *Y10T 29/49863* (2015.01)

(58) Field of Classification Search
CPC .. A61M 5/20; A61M 5/3159; A61M 5/31553; A61M 5/31583; A61M 2005/2407; A61M 5/24; A61M 5/2033
See application file for complete search history.

(56) References Cited

U.S. PATENT DOCUMENTS

| 5,104,380 A | 4/1992 | Holman et al. |
| 7,686,786 B2 * | 3/2010 | Moller .............. A61M 5/14566 604/134 |

(Continued)

FOREIGN PATENT DOCUMENTS

| EP | 2 438 941 A1 | 4/2012 |
| WO | 2006/045526 A1 | 5/2006 |

(Continued)

OTHER PUBLICATIONS

International Search Report, dated Sep. 4, 2013, from corresponding PCT application.

(Continued)

*Primary Examiner* — Aarti B Berdichevsky
(74) *Attorney, Agent, or Firm* — Young & Thompson (57) ABSTRACT

An injection device includes a housing for receiving a syringe or cartridge for containing a medicament; a rotary driveshaft mounted for rotation relative to the housing; and an elongate coiled torsion spring having respective formations at opposite ends thereof, with a first formation being anchored in a seat on the rotary drive shaft and a second formation being anchored in a seat on a reaction component. In use relative rotation of the rotary driveshaft and the reaction component in one angular direction strains the torsion drive spring, and release of the strained torsion drive spring causes expression of medicament from the syringe or cartridge. The torsion spring is longitudinally resiliently compressible between its end formations whereby during assembly of the injection device, the torsion spring may be (Continued)

longitudinally compressed and then rotated, thereby urging the end formations of the torsion drive spring into engagement with the respective seats.

20 Claims, 7 Drawing Sheets (56) References Cited

U.S. PATENT DOCUMENTS

| | | | | |
|---|---|---|---|---|
| 8,608,708 | B2* | 12/2013 | Cowe | A61M 5/20 604/134 |
| 8,702,660 | B2* | 4/2014 | Karlsson | A61M 5/20 604/210 |
| 9,182,000 | B2* | 11/2015 | Harms | A61M 5/20 |
| 9,381,307 | B2* | 7/2016 | Eaton | A61M 5/20 |
| 9,415,165 | B2* | 8/2016 | Cowe | A61M 5/20 |
| 2008/0147005 | A1* | 6/2008 | Moller | A61M 5/14566 604/134 |
| 2011/0092905 | A1* | 4/2011 | Cowe | A61M 5/20 604/135 |
| 2011/0224622 | A1* | 9/2011 | Karlsson | A61M 5/20 604/211 |
| 2012/0089099 | A1* | 4/2012 | Harms | A61M 5/20 604/207 |
| 2013/0046249 | A1* | 2/2013 | Cowe | A61M 5/20 604/211 |
| 2013/0281943 | A1* | 10/2013 | Eaton | A61M 5/20 604/246 |

FOREIGN PATENT DOCUMENTS

| | | |
|---|---|---|
| WO | 2010/029043 A1 | 3/2010 |
| WO | 2010/112559 A1 | 10/2010 |
| WO | 2011/039163 A1 | 4/2011 |
| WO | 2011/045611 A2 | 4/2011 |
| WO | 2011/101377 A1 | 8/2011 |
| WO | 2012/045829 A2 | 4/2012 |

OTHER PUBLICATIONS

GB Search Report, dated Aug. 23, 2012, from corresponding GB application.

* cited by examiner

INJECTION DEVICES USING A RESILIENTLY COMPRESSIBLE TORSION SPRING AS DRIVING FORCE

This invention relates to injection devices and methods of assembly thereof. In particular, but not exclusively, the invention relates to automatic or semi-automatic pen-type injectors where a rotary drive shaft driven by a torsion spring rotates to cause expression of an amount of medicament. The user dials in a dose by rotating a dose setting knob by a desired angular amount, which determines the amount of subsequent rotation of the drive shaft when the device is triggered. Typical examples of such devices include our widely available Autopen® pen injector and other injectors of the types described in U.S. Pat. No. 5,104,380, or in WO2011/045611. It will be appreciated of course that the invention may be used in many other types of injection devices where the opposite ends of a torsion spring are connected to associated components of which one typically remains fixed during dose setting and delivery whilst the other rotates. The term drive shaft is used broadly to cover any elongate member that is rotated in use directly or indirectly by the torsion spring and whose rotation directly or indirectly causes expression of a medicament from the syringe or cartridge. In one example the drive shaft may threadedly engage a plunger element which acts on a piston or bung in the syringe or cartridge. In other examples, the drive shaft may be located elsewhere in the transmission train between the torsion spring and the piston or bung.

In a typical arrangement of a coiled torsion spring a hooked portion is provided at one end, with the other formed as a diametral extension, but the nature of the spring is such that it is not possible for there to be predictable consistent angular orientation between the opposite ends of the springs once formed. In the past therefore, it has been common practice to align and attach the spring by hand to the related components at each end. With the increasing numbers it is not cost-effective to assemble such devices by hand and so some form of automatic assembly is required. A need exists for a spring anchorage arrangement which is well suited for automatic assembly, allowing rapid and reliable assembly by an automated assembly machine.

We have therefore designed an arrangement that avoids a requirement for manual alignment so that the relevant components can be assembled automatically, with a consequence increase in production rates.

Accordingly, in one aspect, this invention provides an injection device including:

a housing for receiving a syringe or cartridge for containing a medicament;

a rotary drive shaft mounted for rotation relative to said housing;

an elongate coiled torsion spring having respective formations at opposite ends thereof, with a first end formation being anchored in a seat on said rotary drive shaft and a second end formation being anchored in a seat on a reaction component, whereby in use relative rotation of said rotary drive shaft and said reaction component in one angular direction strains said torsion spring, and release of said strained torsion spring causes expression of medicament from said syringe or cartridge;

wherein said torsion spring is longitudinally resiliently compressible between the end formations whereby during assembly of said injection device, the torsion spring may be longitudinally compressed and rotated, thereby causing the end formations of the torsion spring to be urged into engagement with said respective seats.

We have found that by providing compression the spring may be readily and reliably anchored to the respective components at its opposite ends upon applying relative rotation.

The torsion spring may exert a longitudinal force on the end formations when it is compressed. Conveniently said torsion spring is compressible by an amount that causes it to exert a force of greater than 0.5N on the formations at its ends when compressed.

The longitudinal compression may, for example, be provided by deformation of (or proximal to) the, or each, end formation. Alternatively, the torsion spring may include at least a region of open coil form.

Although the entire torsion spring could be of open coil form, it is preferred for compactness, and torsion capacity, for there to be a portion of closed coil form. Preferably said torsion spring comprises a plurality of open coil portions interspersed with closed coil portions. Preferably, at least one of the formations on said torsion spring is a hooked element, and the seat with which it is urged into engagement comprises an aperture through which at least a portion of the hooked element may pass, the aperture having an edge surface for being caught in the hooked element when there is relative rotation between the torsion spring and the seat during assembly. The or each hooked element may be of generally U-shaped form, thereby to assist capture of said edge surface.

Conveniently at least one of said respective seats includes a detent arrangement past which the hooked element snaps during assembly.

Preferably said reaction component comprises a collar configured to be rotatable relative to said driveshaft in one direction to strain said spring at least during assembly thereof, the collar having a lock arrangement engageable to prevent rotation thereof in the opposite direction. In one arrangement, designed to allow rewinding of the torsion spring, said lock arrangement may comprise a ratchet arrangement. In another arrangement, intended for disposal after the contents of the syringe or cartridge have been discharged, said collar may comprise first stage location means to hold said collar in a longitudinal position in which it may rotate relative to said rotary drive to strain said spring, and second stage location means which prevents rotation of said drive collar in either direction.

In another aspect, this invention provides a method of assembly of an injection device, the injection device including:

a housing for receiving a syringe or cartridge for containing a medicament;

a rotary driveshaft mounted for rotation;

a reaction component, and an elongate coiled torsion spring having respective formations at opposite end regions thereof for engagement with respective seats on said rotary driveshaft and said reaction component, the method comprising:

disposing said elongate coiled torsion spring between said driveshaft and said reaction component;

effecting relative movement of said rotary driveshaft and said reaction component to cause said torsion spring to compress thereby urging said respective formations into engagement with the driveshaft and the reaction component respectively, and effecting relative rotation of said rotary driveshaft and said reaction component to cause said formations to be engaged and captured by said respective seats.

Conveniently said driveshaft includes a hollow tubular portion and the method comprises inserting said torsion spring into said tubular portion. During assembly said relative rotation is conveniently effected by applying rotation to said reaction component, although rotation could be applied to the driveshaft instead or as well.

In one arrangement said reaction component is rotated against the effect of a ratchet, thereby preventing or limiting angular return movement of the reaction component.

In another arrangement, having rotated the reaction component to strain the torsion drive spring, the reaction component is locked against further rotation.

Conveniently said reaction component is locked by effecting relative longitudinal movement thereof into a locking engagement position.

Whilst the invention has been described above, it extends to any inventive combination of the features set out above on the following description or drawings.

Two embodiments of the invention will now be described by way of example only, reference being made to the accompanying drawings in which:

FIGS. 6(a) and (b) are perspective and side views respectively of a drive assembly of a second embodiment in accordance with this invention in which the device is supplied with the torsion spring fully wound;

Figure 1:
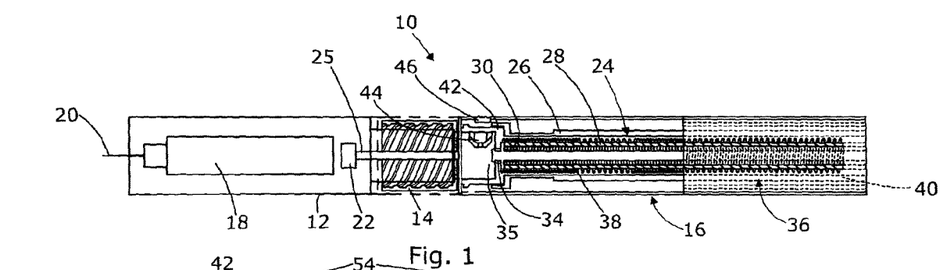
FIG. 1 is a schematic view of a first embodiment of injection device in accordance with this invention.
Figure 2:
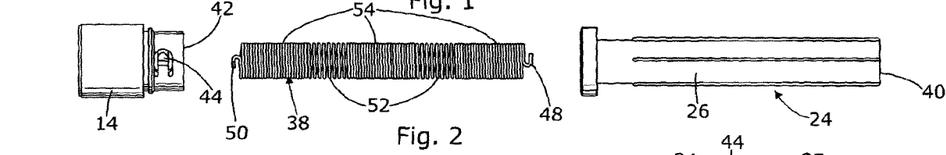
FIG. 2 is a side view showing the driveshaft, torsion spring and rewind collar of the embodiment shown in FIG. 1 before assembly.
Figure 3:
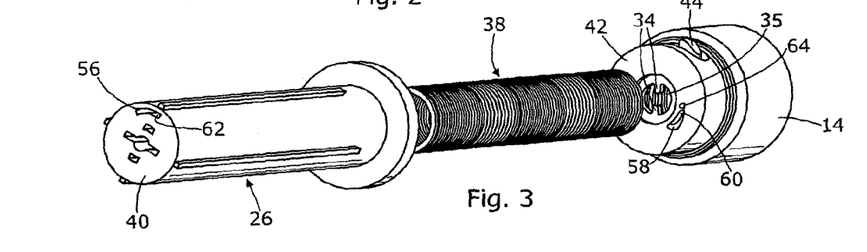
FIG. 3 is a perspective view of the components of FIG. 2.

Referring initially to FIG. 1, the injection device 10 comprises a syringe housing 12 screwed into a rewind collar 14 which is rotatably contained within a drive housing 16. The syringe housing 12 is adapted to receive a syringe 18 having a needle 20 at its forward end and a piston 22 for containing and expressing a medicament through the needle.

The drive housing contains a driveshaft 24 which comprises an outer cylindrical portion 26 and an inner hollow cylindrical mandrel 28 which rotate together. The mandrel has an internal thread 30 at its forward end which engages an external thread on a plunger 32 that operates to push the piston 22 forwardly when the driveshaft rotates. The plunger 25 is provided with two longitudinal key slots which cooperate with teeth 34 in a bore 35 in the rewind collar 14 to prevent rotation of the plunger relative to the housing when the driveshaft rotates. A dose setting and trigger mechanism is indicated generally at 36 and allows a user to dial in a dose value which determines the extent of rotation of the driveshaft 24 under the influence of a torsion spring 38, when the trigger mechanism is released. The dose setting and trigger mechanism may take many forms for example as set forth in U.S. Pat. No. 5,104,380 or WO2011/045611. The torsion spring 38 is disposed in an elongate annular space between the inner and outer cylindrical parts of the driveshaft, anchored at one end to an end wall 40 of the driveshaft 24 and at its other end to an end wall 42 of the rewind collar 14. The torsion spring 38 may be rewound or re-energised by rotating the rewind collar 14 relative to the drive housing 16. The rewind collar 14 has a ratchet tooth 44 which cooperates with a ratchet surface 46 on the drive housing 16 to allow rotation in the rewind direction only.

Referring now more particularly to FIGS. 2 to 5, the construction of the torsion spring 38 and its assembly with the rewind collar 14 and the driveshaft 24 will be described in more detail.

The torsion spring 38 is provided with hook formations 48, 50 at its opposite ends. The hook formations face in opposite angular directions, in each case in the unwinding sense of the spring. Unlike a conventional torsion spring which generally uncompressed and of closed coil form with adjacent coils touching or separated by about 0.5 mn, in this embodiment the torsion spring is provided with two regions 52 of open coil form where the coil spacing is substantially greater, typically 1 mm or more so that the spring is compressible and is under compression once assembled. In the embodiment shown three regions 54 of closed coiled form are interspersed with two regions 52 of open coil form, although many different configurations are possible, including one in which the spring is of open coil form along its full length. Preferably, the region of open coiled form is sufficient to enable the spring to be compressed to exert a force of more than 0.5N when compressed. The driveshaft 24 and the rewind collar 14 are each formed with respective spring seats which comprise apertures in respective end walls 40, 42 of the driveshaft and the rewind collar respectively. Each aperture is designed to lie in the path of the associated hook formation 48, 50 on the torsion spring 38 when the latter is rotated. The apertures are of generally tapered form to provide a gathering effect for the associated hook formation. Although not necessary, the aperture may be necked as shown at 60 so that the hook snaps past the necked region to provide positive capture. The hook formations 48, 50 are designed so as to protrude through the recess and to capture the forward edge 62, 64 of the aperture in the base of the U of the hook formations.

Figure 4A:
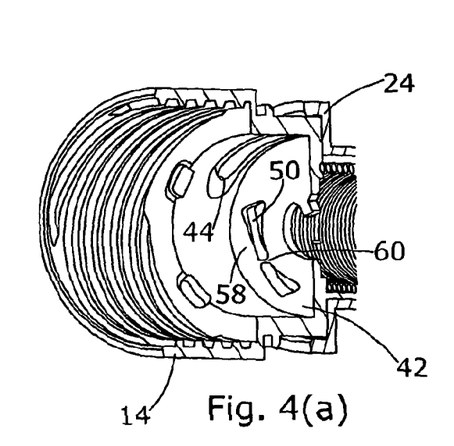
FIGS. 4(a) and (b) are detailed views showing the spring seat on the rewind collar and on the drive shaft respectively with certain parts removed for clarity.
Figure 4B:
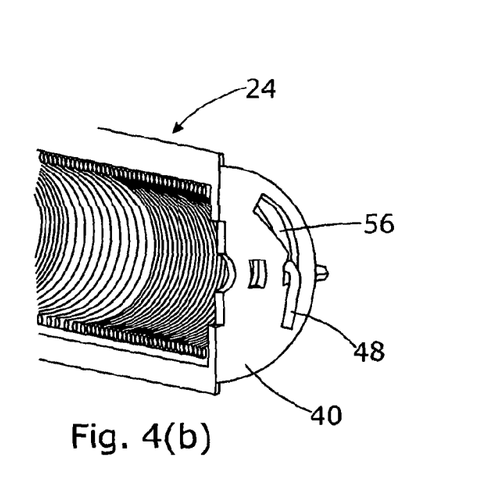
Figure 5A:
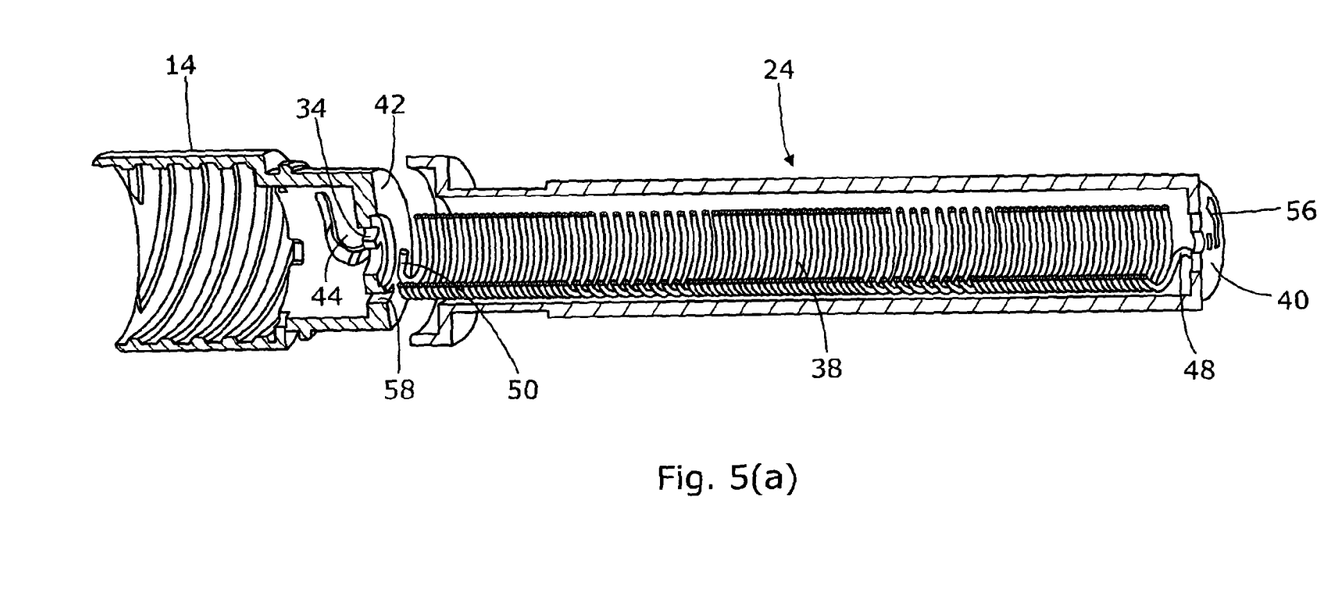
FIG. 5(a) is a side section view showing the driveshaft, the torsion spring and the rewind collar after insertion of the spring into the drive shaft but before compression and rotation thereof, with the inner portion of the drive shaft removed.
Figure 5B:
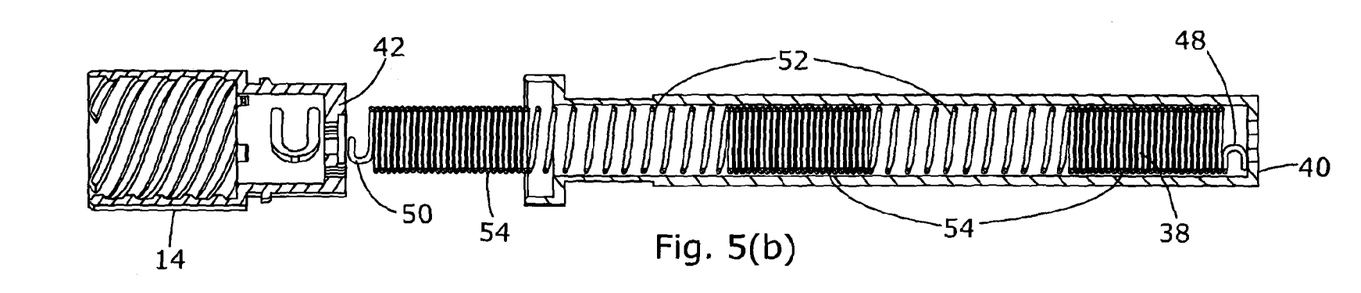
FIGS. 5(b) to (d) are successive views showing compression of the torsion spring and relative rotation of the rewind collar and the driveshaft to finalise the assembly.
Figure 5C:
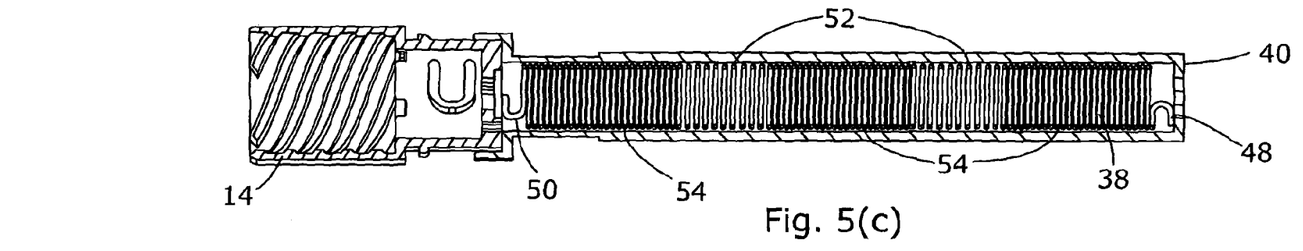
Figure 5D:
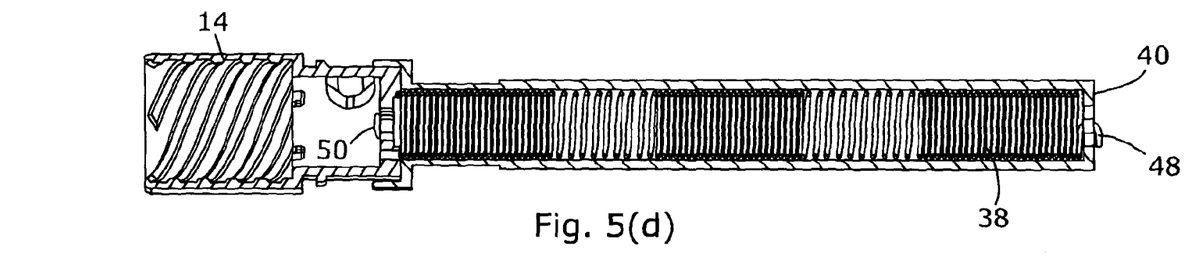

The driveshaft 24, torsion spring 38 and rewind collar 14 are assembled together without requiring any particular prior angular orientation of the torsion spring relative to either the driveshaft or the rewind collar. To assemble these items, the torsion spring 38 is inserted into the driveshaft 24, and the rewind collar 14 is then presented to face the driveshaft as shown in FIGS. 5(a) and (b) with the spring formations being in light contact with the end wall 40 of the driveshaft, and the facing end wall 42 of the rewind collar 14. The rewind collar 14 is then pushed towards the driveshaft 24 so that the opposing faces move into sliding contact as shown in FIGS. 4(a) and 5(c) and thus compressing the torsion spring 38 such that the hook formations 48, 50 are pressed firmly into contact with their respective end walls 40, 42 under the influence of the spring. The rewind collar 14 is then rotated relative to the driveshaft 24 until first one, then the other hook formation 48, 50 passes through the aperture, to seat firmly with the remote parts of the hooked portions passing through the aperture and the edge of the aperture being engaged in the U portions of the hooks as shown in FIGS. 4(a), 4(b) and 5(d). This gives secure engagement and typically is achieved within one rotation of the rewind collar 14 relative to the driveshaft 24. The sub-assembly of the driveshaft, torsion spring and rewind collar may then be assembled automatically with the other components making up the injection device of FIG. 1.

The components within the drive housing in the embodiment of FIGS. 1 to 6, are intended to form a reusable drive assembly which can be reused many times with a fresh or reloadable syringe housing. Once the contents of the syringe have been used (typically after several daily doses) the syringe housing is unscrewed from the drive housing to allow removal and replacement of the syringe. Before reassembling the drive housing and the syringe housing, the drive housing needs to be recharged and this is done by rotating the rewind collar 14 relative to the drive housing to re-energise the spring by rewinding it and simultaneously winding the threaded plunger 25 back into the drive housing 16.

Figures 6A, 6B:
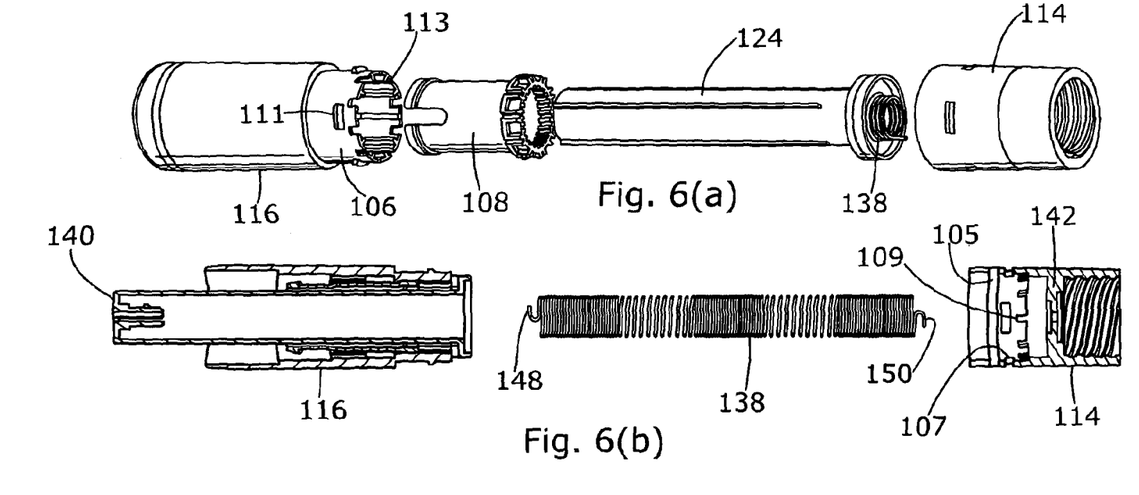
Figures 7A, 7B:
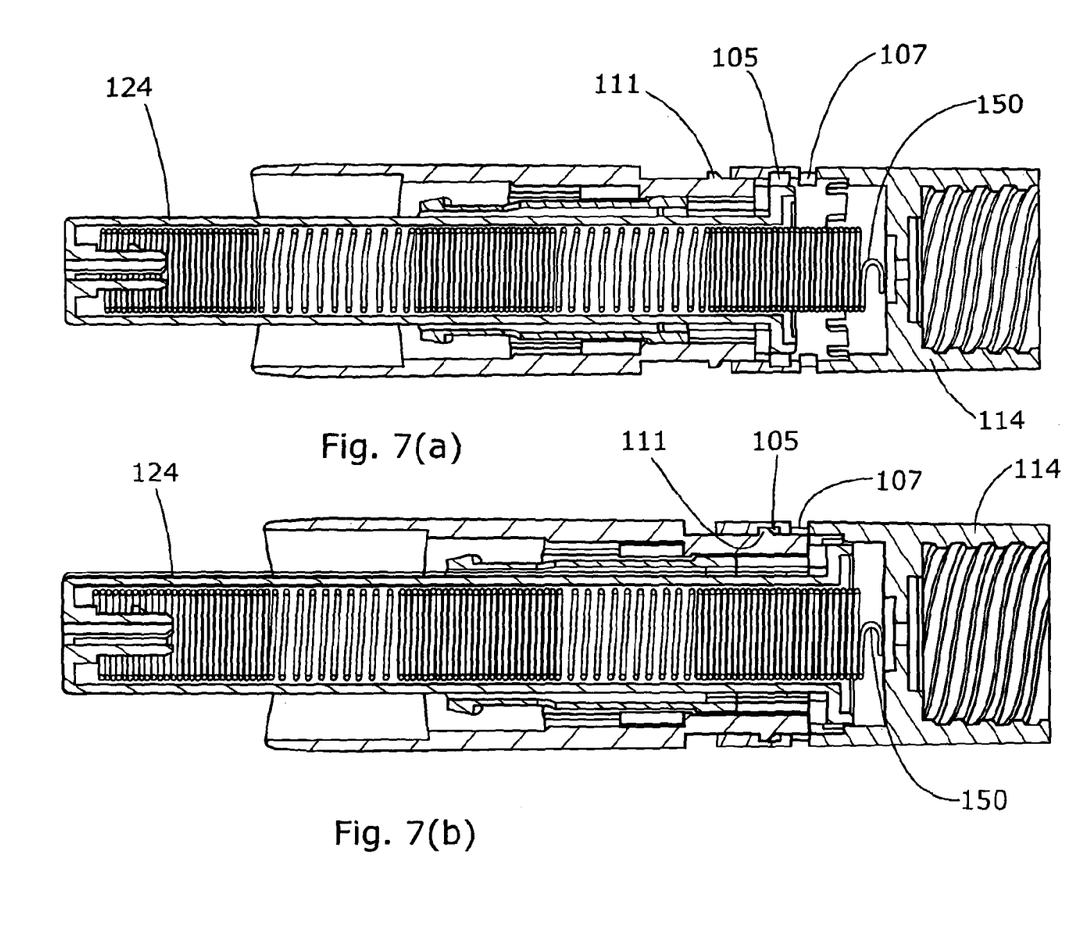
FIGS. 7(a) to (d) are successive views showing insertion of the torsion spring into the driveshaft, moving the reaction collar to a first engagement position for relative rotation, rotation of the collar to capture the ends of the torsion spring and then movement to a final engagement position to lock the reaction collar against further rotation.
Figures 7C, 7D:
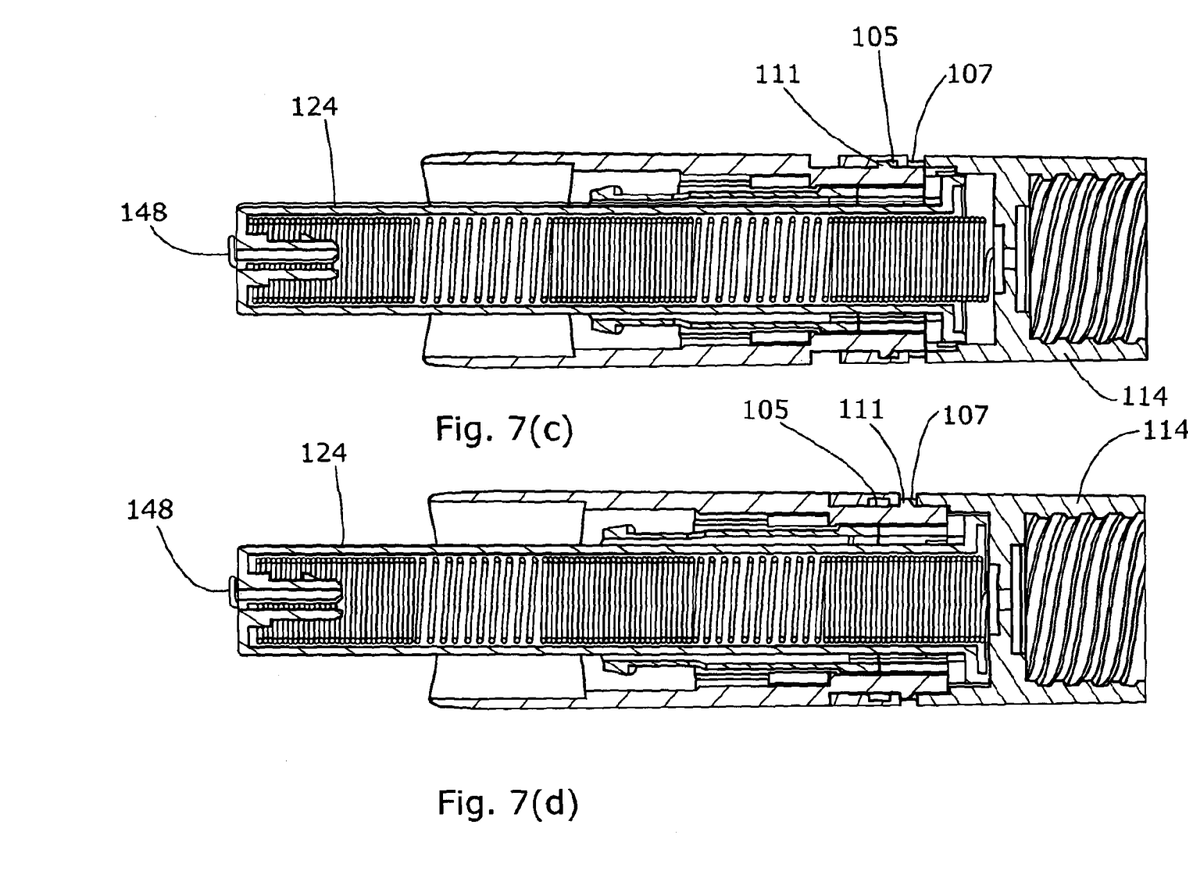

In other arrangements, a rewind facility may not be required, and so the device is supplied to the user with the torsion spring pre-energised, with the device being disposed of once the useable contents of a syringe have been delivered. The embodiment of FIGS. 6 and 7 illustrate a sub-assembly for such a device. The driveshaft and torsion spring are of similar form to those described in relation to the first embodiment. In FIG. 6(a) the sub-assembly is shown comprising a reaction collar 114, a torsion drive spring 138, a driveshaft 124, a dosing and setting clutch 108 and a drive housing 116. It will be noted that the reaction collar 114 has a portion which fits over a corresponding sleeve 106 on the drive housing 116. As seen in FIG. 6(b), the reaction collar has a first stage internal facing circumferential groove 105 spaced from forward recesses 107 forwardly of which are internal castellations 109. The sleeve 106 on the drive portion is provided with four equi-spaced rib segments 111 which cooperation in first stage engagement with the circumferential groove 105 and, in second stage engagement with the four recesses 107. In addition the sleeve 106 on the drive housing 116 has corresponding castellations 113 which engage with the castellations 109 on the reaction collar when the reaction collar 114 and the drive housing 116 are in second stage engagement.

In order to put together the sub-assembly, as previously, the torsion spring 138 is introduced into the interior of the driveshaft 124 in a random angular orientation. The reaction collar 114 is offered up to the drive housing and pushed into a first stage engagement so that the ribs 111 seat in the circumferential groove 105. This holds the reaction collar 114 and the drive housing 116 against longitudinal movement but allows them to rotate relative to each other. In this first stage engagement position, as seen in FIG. 7(b) the torsion spring 138 is compressed, and urges the hook formations 148, 150 into contact with the respective end walls 140, 142. The reaction collar 114 is then rotated, typically through less than one complete turn, which causes engagement of first one and then the other hooks into the seats provided in the reaction collar and the driveshaft as in the previous embodiment. The reaction collar 114 may then be rotated through a required number of turns to energise the torsion spring 138. When sufficiently energised, and this may be determined by counting the number of rotations or by monitoring the torque acting on the reaction component (or both), the reaction collar is locked in this angular position by pushing it fully home to the position shown in FIG. 7(d) where the castellations 113, 109 on the drive housing 116 and the reaction collar 114 engage to prevent relative rotation and the ribs 111 on the drive housing snap through the recesses 107 on the reaction collar to hold the reaction collar in this position.

Although the invention has been described above with reference to one or more preferred embodiments, it will be appreciated that various changes or modifications may be made without departing from the scope of the invention as defined in the appended claims. For example, while the embodiment above is arranged to allow resilient compression of the torsion spring 38 by compression of the two regions 52 of open coil it will be appreciated that there may be alternate ways of modifying a conventional (i.e. substantially uncompressible) torsion spring such that it may act as a compression spring during assembly.

Figure 8:
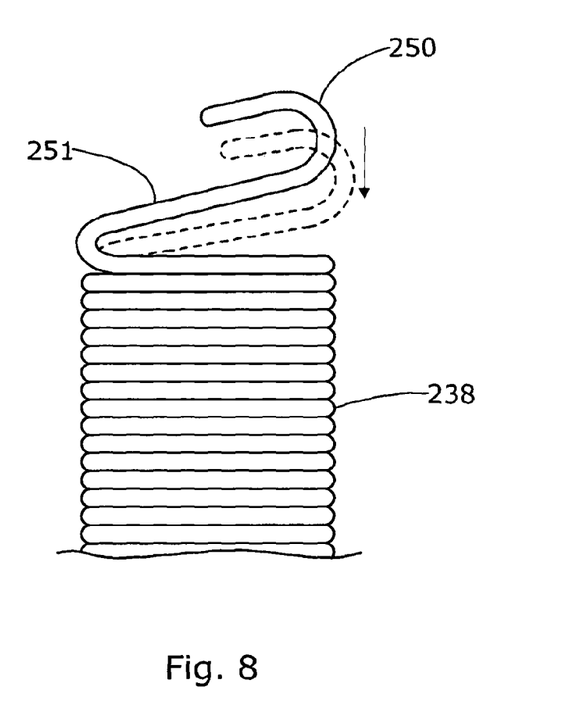
FIG. 8 is a side view of the end formation of a spring suitable for use in embodiments of the invention.

For example, as shown in FIG. 8, a portion of the end formations 250 of the spring 238 may be elastically deformable in the longitudinal direction of the spring 238. While FIG. 8 shows only a single end formation for simplicity it will be appreciated that an embodiment in which the spring does not include an open coil section will typically include deformable end formations at both ends of the spring. Thus, the end formation enables longitudinal compression of the spring by being deformed in the direction of arrow A into a deformed position shown in dashed outline. In this position the end formation will exert a force in the opposite direction to arrow A. Conveniently, for example each end formation 250 may be a hook and the deformation may occur in a connecting portion 251 which extends between the hook and the end of the spring 238. Thus, during assembly the end formations 250 may be compressed against their respective end walls resulting in the may exert a force so as to firmly press the end formations 250 into contact with the end walls.

The invention claimed is:

1. An injection device comprising:
a housing (12) for receiving a syringe (18) or cartridge for containing a medicament;
a rotary drive shaft (24) mounted for rotation relative to said housing (12); and
an elongate coiled torsion spring (38) having respective formations (48, 50) at opposite ends thereof with a first end formation (50) being anchored in a seat (56) on said rotary drive shaft (24) and a second end formation (48) being anchored in a seat (58) on a reaction component (14),
whereby in use relative rotation of said rotary drive shaft (24) and said reaction component (14) in one angular direction strains said torsion spring (38), and release of said strained torsion spring causes expression of medicament from said syringe or cartridge;
wherein said torsion spring is longitudinally resiliently compressible between the first and second end formations whereby during assembly of said injection device, the torsion spring may be longitudinally compressed and rotated, thereby causing the end formations (48, 50) of the torsion spring to be urged into engagement with said respective seats (58, 56).

2. An injection device according to claim 1, wherein said reaction component comprises a collar (14) configured to be rotatable relative to said driveshaft (24) in one direction to strain said torsion spring (38), the collar (14) having a lock arrangement (44, 46) to prevent rotation thereof in the opposite direction.

3. An injection device according to claim 2, wherein said collar (114) comprises first stage location means (111, 105)

to hold said collar in a longitudinal position in which it may rotate relative to said rotary drive to strain said spring, and a second stage location means (111, 117) which prevents rotation of said collar (14) in either direction.

4. An injection device according to claim 2, wherein said lock arrangement comprises a ratchet arrangement (44, 46).

5. An injection device according to claim 1, wherein said torsion spring includes at least a region (52) of open coil form.

6. An injection device according to claim 5, wherein said torsion spring includes a region (54) of closed coil form.

7. An injection device according to claim 5, wherein at least one of the formations (48, 50) on said torsion spring is a hooked element and the seat (58, 56) with which it is urged into engagement comprises an aperture through which at least a portion of the hooked element may pass, the aperture having an edge surface for being caught in the hooked element when there is relative rotation between the torsion drive spring and the seat during assembly.

8. An injection device according to claim 1, wherein said torsion spring includes a region (54) of closed coil form.

9. An injection device according to claim 8, wherein at least one of the formations (48, 50) on said torsion spring is a hooked element and the seat (58, 56) with which it is urged into engagement comprises an aperture through which at least a portion of the hooked element may pass, the aperture having an edge surface for being caught in the hooked element when there is relative rotation between the torsion drive spring and the seat during assembly.

10. An injection device according to claim 8, wherein said torsion spring (38) comprises a plurality of open coil regions (52) interspersed with closed coil regions (54).

11. An injection device according to claim 1, wherein at least one of the formations (48, 50) on said torsion spring is a hooked element and the seat (58, 56) with which it is urged into engagement comprises an aperture through which at least a portion of the hooked element may pass, the aperture having an edge surface for being caught in the hooked element when there is relative rotation between the torsion drive spring and the seat during assembly.

12. An injection device according to claim 11, wherein said hooked elements (48, 50) are of generally U-shaped form thereby to assist capture of said edge surface.

13. An injection device according to claim 11, wherein at least one of said respective seats (56, 58) includes a detent arrangement (60) past which the hooked element (48, 50) snaps during assembly.

14. An injection device including:
a housing (12) for receiving a syringe (18) or cartridge for containing a medicament;
a rotary drive shaft (24) mounted for rotation relative to said housing (12);
an elongate coiled torsion spring (38) having respective formations (48, 50) at opposite ends thereof with a first end formation (50) being anchored in a seat (56) on said rotary drive shaft (24) and a second end formation (48) being anchored in a seat (58) on a reaction component (14),
whereby in use relative rotation of said rotary drive shaft (24) and said reaction component (14) in one angular direction strains said torsion spring (38), and release of said strained torsion spring causes expression of medicament from said syringe or cartridge;
wherein said torsion spring includes at least a region of open coil form whereby during assembly of said injection device, the torsion spring may be longitudinally compressed and rotated, thereby causing the end formations (48, 50) of the torsion spring to be urged into engagement with said respective seats (58, 56).

15. A method of assembly of an injection device, the injection device including:
a housing (12, 16) for receiving a syringe or cartridge (18) for containing a medicament;
a rotary driveshaft mounted for rotation (24);
a reaction component (14), and
an elongate coiled torsion spring (38) having respective formations (48, 50) at opposite end regions thereof for engagement with respective seats (58, 56) on said rotary driveshaft and said reaction component respectively,
the method comprising:
disposing said elongate coiled torsion spring (38) between said driveshaft (24) and said reaction component (14);
effecting relative movement of said rotary driveshaft and said reaction component to cause said torsion spring to compress thereby urging said respective formations (48, 50) into engagement with the driveshaft and the reaction component respectively, and
effecting relative rotation of said rotary driveshaft and said reaction component to cause said formations (48, 50) to be engaged and captured by said respective seats (58, 56).

16. A method according to claim 15, wherein said elongate driveshaft (24) includes a hollow tubular portion and the method comprises inserting said elongate coiled torsion spring (38) into said tubular portion.

17. A method according to claim 15, wherein said relative rotation is affected by applying rotation to said reaction component (14).

18. A method according to claim 17, wherein said reaction component (14) is rotated against the effect of a ratchet (44, 46), thereby preventing return movement of the return angular movement of the reaction component.

19. A method according to claim 17, wherein, having rotated the reaction component (114) to strain the torsion drive spring (138), the reaction component is locked against further rotation.

20. A method according to claim 19, wherein said reaction component (114) is locked by effecting relative longitudinal movement thereof into a locking engagement position (109, 111).

* * * * *